United States Patent [19]

Robertson

[11] Patent Number: 4,591,591
[45] Date of Patent: May 27, 1986

[54] PYRIDAZINONE DERIVATIVES AS INOTROPIC AGENTS

[75] Inventor: David W. Robertson, Indianapolis, Ind.

[73] Assignee: Eli Lilly and Company, Indianapolis, Ind.

[21] Appl. No.: 587,732

[22] Filed: Mar. 8, 1984

[51] Int. Cl.⁴ .................. A61K 31/50; A61K 31/495; A61K 31/535

[52] U.S. Cl. .................................... 514/254; 514/229; 514/234; 514/237; 514/239

[58] Field of Search ................ 424/250, 248.57, 248.4; 514/254, 229, 234, 237, 239

[56] References Cited

U.S. PATENT DOCUMENTS

| | | | |
|---|---|---|---|
| 3,845,050 | 10/1974 | Lebkuecher et al. | 260/250 A |
| 4,258,185 | 3/1981 | Nakao et al. | 544/114 |
| 4,304,777 | 12/1981 | Lesher et al. | 424/250 |
| 4,353,905 | 10/1982 | Sircar et al. | 424/250 |
| 4,361,563 | 11/1982 | Austel et al. | 424/250 |
| 4,397,854 | 8/1983 | Sircar | 424/250 |
| 4,404,203 | 9/1983 | Sircar | 424/250 |

FOREIGN PATENT DOCUMENTS 68310  1/1983  European Pat. Off. .

OTHER PUBLICATIONS

Curran et al., *J. Med. Chem.*, 17(3), 273 (1974).
McEvoy et al., *J. Med. Chem.*, 17(3), 281 (1974).
Derwent 27593K/12 Abstracting German OLS No. 3,135,617.
Derwent 18918K/08 Abstracting Japanese Pat. No. J58008016.

*Primary Examiner*—Allen J. Robinson
*Attorney, Agent, or Firm*—Charles W. Ashbrook; Arthur R. Whale

[57] ABSTRACT

This invention provides for the use of certain pyridazinones as positive inotropic agents.

8 Claims, No Drawings

PYRIDAZINONE DERIVATIVES AS INOTROPIC AGENTS

BACKGROUND OF THE INVENTION

The cardiac glycosides and the sympathomimetic amines are the principal inotropic agents used in the management of congestive heart failure. Although the cardiac glycosides, especially digitalis, are among the most frequently prescribed drugs, they have numerous liabilities such as a low therapeutic index and erratic absorption, and are associated with life-threatening arrhythmias and deleterious drug-drug interactions. In addition, many patients either do not respond, or become refractory to these agents. The sympathomimetic amines, such as dopamine and epinephrine, have limited utility due to positive chronotropic effects, arrhythmogenic properties, and oral ineffectiveness.

More recently, new classes of inotropic agents have been found. These include certain dihydropyridazinone derivatives such as these taught in U.S. Pat. Nos. 4,353,905, 4,361,563, 4,304,777, and 4,404,203 which cause an increase in myocardial contractility in anesthetized dogs and cats. Other pyridazinone derivatives are taught in the art to be cardiotonics, antihypertensives, and antithrombotic agents.

U.S. Pat. No. 4,258,185 teaches the compounds used in the present invention as antithrombotic and antihypertensive drugs.

The present invention provides for the use of certain pyridazinone derivatives as potent, long-acting orally effective positive inotropic agents which have minimal effects on blood pressure and heart rate.

SUMMARY OF THE INVENTION

This invention provides for a method of treating a mammal, including a human subject, suffering from or susceptible to heart failure, which comprises administering to said mammal an effective amount of a compound of Formula I

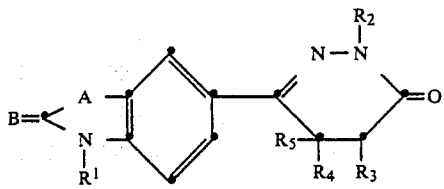

or a pharmaceutically acceptable salt thereof, wherein

A is methylene, ethylene, $C_1$-$C_4$ alkyl substituted ethylene, vinylene, or $C_1$-$C_4$ alkyl substituted vinylene;

B=C< is O=C< or $H_2$C<;

$R_1$ is hydrogen, $C_1$-$C_4$ alkyl, $C_2$-$C_4$ alkanoyl, methyl- or ethyl-sulfonyl, or benzoyl optionally substituted on the phenyl ring with one or more substituents selected from halogen, $C_1$-$C_4$ alkyl, methoxy or ethoxy;

$R_2$ is hydrogen, $C_1$-$C_{22}$ alkyl, hydroxy-substituted $C_1$-$C_3$ alkyl, carbamoyl-substituted $C_1$-$C_{11}$ alkyl, naphthyloxy-methyl or -ethyl, an oxoalkyl group or $R_6R_7N$—$(CH_2)_n$— where each of $R_6$ and $R_7$ is independently hydrogen or $C_1$-$C_4$ alkyl, or when taken together with the nitrogen atom to which they are attached form a pyrrolidine, piperidine, morpholine, piperazine, or N-methylpiperazine ring, and n is 2 or 3;

$R_3$ is hydrogen;

$R_4$ is hydrogen, $C_1$-$C_4$ alkyl, hydroxymethyl, or $C_2$-$C_4$ alkanoyloxymethyl;

$R_5$ is hydrogen or $C_1$-$C_4$ alkyl;

or $R_3$ and one of $R_4$ and $R_5$ taken together form a bond.

DETAILED DESCRIPTION AND PREFERRED EMBODIMENT

The compounds of Formula I are taught and claimed in U.S. Pat. No. 4,258,185 which is expressly incorporated into this application by reference. The terminology used in this application is generally the same as used in the abovenamed patent and the compounds described therein should be considered to be coextensive with those of this application. The compounds as claimed are taught to be biologically useful as inhibitors of platelet aggregation and as antihypertensive agents. No utility directed toward their use as inotropic agents is disclosed or inferred.

A preferred group of compounds are those wherein
(a) B=C< is O=C<;
(b) A is methylene, ethylene, or lower alkyl substituted ethylene;
(c) each of $R_1$, $R_2$, $R_3$, and one of $R_4$ and $R_5$ is hydrogen; and
(d) the other of $R_4$ and $R_5$ is hydrogen or methyl.

Especially preferred are 1,3-dihydro-5-(1,4,5,6-tetrahydro-6-oxo-3-pyridazinyl)-2H-indol-2-one, 1,3-dihydro-5-(1,4,5,6-tetrahydro-4-methyl-6-oxo-3-pyridazinyl)-2H-indol-2-one, 1,2,3,4-tetrahydro-6-(1,4,5,6-tetrahydro-6-oxo-3-pyridazinyl)quinolin-2-one, and 1,2,3,4-tetrahydro-6-(1,4,5,6-tetrahydro-4-methyl-6-oxo-3-pyridazinyl)quinolin-2-one, or pharmaceutically acceptable salts thereof.

The compounds may be administered by various routes including the oral, rectal, transdermal, subcutaneous, intravenous, intramuscular, or intranasal routes, being usually employed in the form of a pharmaceutical composition. It is a special feature of these compounds that they are effective and long acting positive inotropic agents following oral administration.

The active compounds are effective over a wide dosage range. For example, dosages per day will normally fall within the range of about 0.5 to 300 mg./kg. of body weight. In the treatment of adult humans, the range of about 1 to 50 mg./kg., in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way. The compounds of Formula I are particularly useful as inotropic agents due to their potency, long action of effect, and oral efficacy. Certain compounds of Formula I were examined as to their pharmacodynamic effects in the following test systems.

Positive Inotropic Activity in Isolated Cat Papillary Muscles

Cats of either sex were anesthetized with Metofane (1,1-difluoro-2,2-dichloroethyl methyl ether, Pittman-Moore) their hearts immediately removed and the papillary muscles dissected and suspended in individual organ baths. A platinum hook secured on one of the muscle to an electrode mounted in the bottom of the bath, and a silk thread attached the tendon to a Statham isometric transducer. The baths contained Krebs-Henseleit solution (36° C., bubbled with 95 percent oxygen-5 percent carbon dioxide) of the following millimolar composition: NaCl, 118; KCl, 4.5; CaCl$_2$, 2.5; KH$_2$PO$_4$, 1.1; MgSO$_4$, 1.2; NaHCO$_3$, 25; and glucose, 11.

A base-line tension of 1.5 g. was applied to each muscle. Square-wave pulses (5.0 msec. in duration, three times threshold voltage) delivered through the hook electrode and a second electrode positioned near the top of the muscle evoked 12 contractions/minute, which were recorded on a Grass polygraph. After the muscles had equilibrated for 60 minutes, the recorder gain was adjusted so that the pen deflected 10 mm. The drug was introduced in a solution of normal saline in an amount to bring the final concentration of the drug to $10^{-5}$ or $10^{-4}$ molar. Increases in contractility were tabulated as millimeters of pen deflection in excess of the baseline value. In each experiment the maximum contractility was measured. Test results are summarized in Table I and are expressed as percent of control (control=100 percent). Values are the average of results from 2 to 8 muscles.

Test Compounds

A.         1,3-dihydro-5-(1,4,5,6-tetrahydro-6-oxo-3-pyridazinyl)-2H-indol-2-one
B.     1,2,3,4-tetrahydro-6-(1,4,5,6-tetrahydro-6-oxo-3-pyridazinyl)quinolin-2-one

TABLE I

| Effects of Compounds of Formula I on Contractility in Cat Papillary Muscles | | |
|---|---|---|
| | Contractility of Papillary Muscle* Drug Concentration | |
| Test Compound | $10^{-5}$ M | $10^{-4}$ M |
| A | 147 | 152 |
| B | 154 | 150 |

*Data are peak responses at the indicated concentration of drug and are expressed as a percent of control (control = 100 percent).

Experiments in Anesthetized Dogs

Mongrel dogs of either sex ranging in weight from 7 to 14 l kg. were used. Anesthesia was induced with sodium pentobarbital (30 mg./kg., i.v.) and maintained with supplemental doses as required. A positive-pressure pump was used to ventilate the dogs through an endotracheal tube (18 strokes/minute, 20 ml./kg. stroke$^{-1}$), and a heating pad kept the body temperature at 37°-38° C.

Femoral arterial blood pressure was measured through a polyethylene catheter filled with heparin solution (16 units/ml.) and connected to a Statham pressure transducer. A strain-gauge arch sutured to the right ventricle of the heart measured cardiac contractility. Tension on the gauge was adjusted to 50 g. and the gain of the recorder (Beckman dynograph) was set so that 50 g. caused a 10-mm. pen deflection; cardiac contractile tension was measured as millimeters of pen deflection or grams of tension. The drug was administered following a 30-45 minute equilibrium period as an i.v. bolus (2-5 ml.) in a normal saline vehicle. In a control experiment, rapid intravenous injection of 50 ml. of 5 percent dextran and mechanical compression of the aorta showed that the contractility measurements were independent of changes in preload and afterload. Heart rate was derived by means of a cardiotach which was triggered by the arterial pressure pulse signal and displayed on the polygraph. The maximum effects on contractility at various dose levels were determined and plotted and the dose required to produce a 50% increase in contractility (ED$_{50}$) was determined by interpolation. The ED$_{50}$'s for each compound tested are summarized in Table II.

TABLE II

| Effects of Compounds of Formula I on Ventricular Contractility in the Anesthetized dog | |
|---|---|
| Test Compound | ED$_{50}$ (mcg./kg.)* |
| A | 10 |
| B | 5 |

*i.v. dose required to produce a peak increase in contractility of 50%.

I claim:

1. A method of treating a mammal, including a human subject, suffering from heart failure, which comprises administering to said mammal an effective amount of a compound of the formula

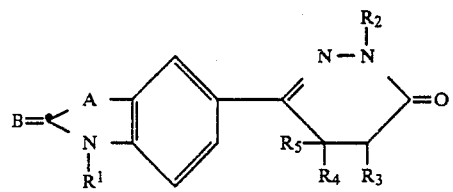

or a pharmaceutically acceptable salt thereof, wherein
A is methylene, ethylene, C$_1$–C$_4$ alkyl substituted ethylene, vinylene, or C$_1$–C$_4$ alkyl substituted vinylene;
R$_1$ is hydrogen, C$_1$–C$_4$ alkyl, C$_2$–C$_4$ alkanoyl, methyl- or ethyl-sulfonyl, or benzoyl optionally substituted on the phenyl ring with one or more substituents selected from the group consisting of halogen, C$_1$–C$_4$ alkyl, methoxy and ethoxy;
R$_2$ is hydrogen, C$_1$–C$_{22}$ alkyl, hydroxy-substituted C$_1$–C$_3$ alkyl, carbamoyl-substituted C$_1$–C$_{11}$ alkyl, naphthyloxymethyl or -ethyl, a C$_1$–C$_5$ oxoalkyl group or R$_6$R$_7$N—(CH$_2$)$_n$— where each of R$_6$ and R$_7$ is independently hydrogen or C$_1$–C$_4$ alkyl, or when taken together with the nitrogen atom to which they are attached form a pyrrolidine, piperidine, morpholine, piperazine, or N-methylpiperazine ring, and n is 2 or 3;
R$_3$ is hydrogen;
R$_4$ is hydrogen, C$_1$–C$_4$ alkyl, hydroxymethyl, or C$_2$–C$_4$ alkanoyloxymethyl;
R$_5$ is hydrogen or C$_1$–C$_4$ alkyl;
or R$_3$ and one of R$_4$ and R$_5$ taken together form a bond.

2. A method according to claim 1 wherein each of R$_1$, R$_2$, and R$_3$ is hydrogen.

3. A method according to claim 2 wherein A is methylene.

4. The method of claim 3 wherein the compound is 1,3-dihydro-5-(1,4,5,6-tetrahydro-6-oxo-3-pyridazinyl)-2H-indol-2-one or a pharmaceutically acceptable salt thereof.

5. The method of claim 3 wherein the compound is 1,3-dihydro-5-(1,4,5,6-tetrahydro-4-methyl-6-oxo-3-pyridazinyl)-2H-indol-2-one or a pharmaceutically acceptable salt thereof.

6. A method according to claim 2 wherein A is ethylene.

7. A method according to claim 6 wherein the compound is 1,2,3,4-tetrahydro-6-(1,4,5,6-tetrahydro-6-oxo-3-pyridazinyl)quinolin-2-one or a pharmaceutically acceptable salt thereof.

8. A method according to claim 6 wherein the compound is 1,2,3,4-tetrahydro-6-(1,4,5,6-tetrahydro-4-methyl-6-oxo-3-pyridazinyl)quinolin-2-one or a pharmaceutically acceptable salt thereof.

* * * * *

UNITED STATES PATENT AND TRADEMARK OFFICE
CERTIFICATE OF CORRECTION

PATENT NO. : 4,591,591
DATED : May 27, 1986
INVENTOR(S) : David W. Robertson

It is certified that error appears in the above—identified patent and that said Letters Patent is hereby corrected as shown below:

Column 4, line 35, after "nylene;" insert in a new line
-- B=C< is O=C<; --

Signed and Sealed this

Third Day of February, 1987

Attest:

DONALD J. QUIGG

Attesting Officer

Commissioner of Patents and Trademarks